United States Patent
Thrash et al.

(10) Patent No.: US 10,040,990 B1
(45) Date of Patent: Aug. 7, 2018

(54) HYDRAULIC FRACTURE COMPOSITION AND METHOD

(71) Applicant: Superior Silica Sands, LLC, Ft. Worth, TX (US)

(72) Inventors: Tommy K. Thrash, Lubbock, TX (US); Calder Hendrickson, Lubbock, TX (US)

(73) Assignee: AQUASMART ENTERPRISES, LLC

( * ) Notice: Subject to any disclaimer, the term of this patent is extended or adjusted under 35 U.S.C. 154(b) by 0 days.

(21) Appl. No.: 15/014,623

(22) Filed: Feb. 3, 2016

Related U.S. Application Data

(63) Continuation of application No. 14/171,920, filed on Feb. 4, 2014, which is a continuation of application No. 13/418,227, filed on Mar. 12, 2012, now Pat. No. 9,057,014, which is a continuation-in-part of application No. 13/299,288, filed on Nov. 17, 2011, now Pat. No. 8,661,729, which is a continuation-in-part of application No. 12/789,177, filed on May 27, 2010, now Pat. No. 8,341,881, which is a continuation of application No. 12/327,608, filed on Nov. 26, 2008, now Pat. No. 7,726,070.

(60) Provisional application No. 61/012,912, filed on Dec. 11, 2007.

(51) Int. Cl.
*C09K 8/80* (2006.01)

(52) U.S. Cl.
CPC .................. *C09K 8/805* (2013.01)

(58) Field of Classification Search
None
See application file for complete search history.

(56) References Cited

U.S. PATENT DOCUMENTS

| | | | | |
|---|---|---|---|---|
| 336,979 A | * | 3/1886 | Ingraham et al. | B02C 4/10 241/142 |
| 2,690,388 A | | 9/1954 | Hale | |
| 2,765,291 A | | 10/1956 | Horne | |
| 2,967,789 A | | 1/1961 | Hoyt | |

(Continued)

FOREIGN PATENT DOCUMENTS

| | | |
|---|---|---|
| DE | 4224368 A1 | 1/1994 |
| DE | 19936028 A1 | 2/2001 |

(Continued)

OTHER PUBLICATIONS

Drill & Fill Manufacturing. Turf Tractor Specifications. http://www.drillandfillmfg.com/tractor.html. Accessed May 27, 2008.

(Continued)

*Primary Examiner* — Jeffrey Washville
(74) *Attorney, Agent, or Firm* — Pate Baird, PLLC

(57) ABSTRACT

A method for improving the performance of fracturing processes in oil production fields may rely on polymer coated particles carried in the fracturing fluid. The particles may include heavy substrates, such as sand, ceramic sand, or the like coated with polymers selected to absorb water, increasing the area and volume to travel more readily with the flow of fluid without settling out, or allowing the substrate to settle out. Ultimately, the substrate may become lodged in the fissures formed by the pressure or hydraulic fracturing, resulting in propping open of the fissures for improved productivity.

7 Claims, 6 Drawing Sheets

(56) References Cited

U.S. PATENT DOCUMENTS

| | | |
|---|---|---|
| 2,991,267 A | 7/1961 | Bean |
| 3,336,129 A | 8/1967 | Herrett et al. |
| 3,336,979 A | 8/1967 | Ingraham et al. |
| 3,353,601 A | 11/1967 | Dollarhide et al. |
| 3,442,803 A | 5/1969 | Hoover et al. |
| 3,648,631 A | 3/1972 | Fiedler et al. |
| 3,705,467 A | 12/1972 | McKnight |
| 3,752,233 A | 8/1973 | Knight |
| 3,768,565 A | 10/1973 | Persinski et al. |
| 3,841,402 A | 10/1974 | Knight et al. |
| 3,868,328 A | 2/1975 | Boothe et al. |
| 3,943,060 A | 3/1976 | Martin et al. |
| 3,973,355 A | 8/1976 | McKenzie |
| 4,104,824 A | 8/1978 | Lundberg et al. |
| 4,172,066 A | 10/1979 | Lamphere et al. |
| 4,187,803 A | 2/1980 | Valenta et al. |
| 4,195,010 A | 3/1980 | McClinton et al. |
| 4,247,331 A | 1/1981 | Hamlin et al. |
| 4,272,417 A | 6/1981 | Barke et al. |
| 4,473,689 A | 9/1984 | Login et al. |
| 4,540,427 A | 9/1985 | Helbling |
| 4,579,578 A | 4/1986 | Cooke |
| 4,762,545 A | 8/1988 | Youssef et al. |
| 4,829,100 A | 5/1989 | Murphey et al. |
| 4,942,186 A | 7/1990 | Murphey et al. |
| 5,013,349 A | 5/1991 | Tanaka |
| 5,093,130 A | 3/1992 | Fujii et al. |
| 5,128,390 A | 7/1992 | Murphey et al. |
| 5,394,812 A | 3/1995 | Dunning et al. |
| 5,420,174 A | 5/1995 | Dewprashad |
| 5,450,985 A | 9/1995 | Meuleman |
| 5,501,274 A | 3/1996 | Nguyen et al. |
| 5,554,446 A | 9/1996 | Minder et al. |
| 5,633,220 A | 5/1997 | Cawiezel et al. |
| 5,794,550 A | 8/1998 | Chadwick |
| 5,806,593 A | 9/1998 | Surles |
| 5,921,317 A | 7/1999 | Dewprashad et al. |
| 5,951,978 A | 9/1999 | Red'kina et al. |
| 5,981,446 A | 11/1999 | Qiu et al. |
| 6,076,299 A | 6/2000 | Spittle et al. |
| 6,169,058 B1 | 1/2001 | Le et al. |
| 6,329,319 B1 | 12/2001 | Puglisi et al. |
| 6,395,051 B1 | 5/2002 | Arnold et al. |
| 6,454,003 B1 | 9/2002 | Chang et al. |
| 6,528,157 B1 | 3/2003 | Hussain et al. |
| 6,669,752 B2 | 12/2003 | Arnold et al. |
| 6,703,469 B2 | 3/2004 | Sanders et al. |
| 6,710,019 B1 | 3/2004 | Sawdon et al. |
| 6,729,402 B2 | 5/2004 | Chang et al. |
| 6,884,754 B1 | 4/2005 | Schlatter et al. |
| 6,984,705 B2 | 1/2006 | Chang et al. |
| 7,135,231 B1 | 11/2006 | Sinclair et al. |
| 7,156,194 B2 | 1/2007 | Nguyen |
| 7,216,705 B2 | 5/2007 | Saini et al. |
| 7,244,492 B2 | 7/2007 | Sinclair et al. |
| 7,334,640 B2 | 2/2008 | Hanes, Jr. et al. |
| 7,504,445 B2 | 3/2009 | Collin |
| 7,510,656 B2 | 3/2009 | Shafer et al. |
| 7,527,736 B2 | 5/2009 | Shafer et al. |
| 7,595,280 B2 | 9/2009 | Welton et al. |
| 7,628,919 B2 | 12/2009 | Shafer et al. |
| 7,635,404 B1 | 12/2009 | Devic et al. |
| 7,722,770 B2 | 5/2010 | Shafer et al. |
| 7,726,070 B2 | 6/2010 | Thrash |
| 7,814,980 B2 | 10/2010 | Bryant et al. |
| 7,819,192 B2 | 10/2010 | Weaver et al. |
| 7,888,297 B2 | 2/2011 | Hanes, Jr. et al. |
| 7,897,546 B2 | 3/2011 | Showalter et al. |
| 7,989,391 B2 | 8/2011 | Tang et al. |
| 8,082,994 B2 | 12/2011 | Nguyen et al. |
| 8,196,346 B2 | 6/2012 | Thrash |
| 8,341,881 B2 | 1/2013 | Thrash |
| 8,354,360 B2 | 1/2013 | Phatak |
| 8,453,377 B2 | 6/2013 | Thrash et al. |
| 8,510,986 B2 | 8/2013 | Thrash |
| 8,579,028 B2 | 11/2013 | Nguyen et al. |
| 8,739,464 B2 | 6/2014 | Thrash |
| 8,881,453 B2 | 11/2014 | Hendrickson et al. |
| 8,931,209 B2 | 1/2015 | Hendrickson et al. |
| 8,931,210 B2 | 1/2015 | Thrash |
| 9,174,885 B2 | 11/2015 | Taulbee |
| 2001/0001312 A1 | 5/2001 | Mitchell et al. |
| 2001/0002386 A1 | 5/2001 | Steele et al. |
| 2002/0048676 A1 | 4/2002 | McDaniel et al. |
| 2002/0049291 A1 | 4/2002 | Sanders et al. |
| 2003/0046865 A1 | 3/2003 | Nishiyama |
| 2004/0011102 A1 | 1/2004 | Sears |
| 2004/0023809 A1 | 2/2004 | Wertz et al. |
| 2004/0023818 A1 | 2/2004 | Nguyen et al. |
| 2004/0045712 A1 | 3/2004 | Eoff et al. |
| 2004/0049980 A1 | 3/2004 | Principe et al. |
| 2004/0069031 A1 | 4/2004 | Krysiak et al. |
| 2004/0069032 A1 | 4/2004 | Krysiak et al. |
| 2004/0074271 A1 | 4/2004 | Krysiak et al. |
| 2004/0236295 A1 | 11/2004 | Muthiah et al. |
| 2004/0244978 A1 | 12/2004 | Shaarpour |
| 2005/0005869 A1 | 1/2005 | Fritter et al. |
| 2005/0016732 A1 | 1/2005 | Brannon et al. |
| 2005/0019574 A1 | 1/2005 | McCrary |
| 2005/0033256 A1 | 2/2005 | Schmidt et al. |
| 2005/0069566 A1 | 3/2005 | Tamarkin et al. |
| 2005/0076536 A1 | 4/2005 | Hatfield et al. |
| 2005/0173117 A1 | 8/2005 | Roddy |
| 2005/0194141 A1 | 9/2005 | Sinclair et al. |
| 2006/0007922 A1 | 1/2006 | Boys |
| 2006/0047068 A1 | 3/2006 | Doane et al. |
| 2006/0048944 A1 | 3/2006 | van Batenburg et al. |
| 2006/0078682 A1 | 4/2006 | McDaniel et al. |
| 2006/0089266 A1 | 4/2006 | Dusterhoft et al. |
| 2006/0175059 A1 | 8/2006 | Sinclair et al. |
| 2006/0178271 A1* | 8/2006 | Lynch .............. A01N 25/12 504/363 |
| 2006/0211580 A1 | 9/2006 | Wang et al. |
| 2006/0240983 A1 | 10/2006 | Yamaguchi |
| 2006/0255490 A1 | 11/2006 | Gaytan |
| 2007/0036977 A1 | 2/2007 | Sinclair et al. |
| 2007/0051148 A1 | 3/2007 | Terenzio |
| 2007/0066754 A1 | 3/2007 | Loeker et al. |
| 2007/0074315 A1 | 3/2007 | Collin |
| 2007/0093387 A1 | 4/2007 | Sumi et al. |
| 2007/0114030 A1 | 5/2007 | Todd et al. |
| 2007/0114035 A1 | 5/2007 | Parris et al. |
| 2008/0045422 A1 | 2/2008 | Hanes et al. |
| 2008/0064614 A1 | 3/2008 | Ahrenst et al. |
| 2008/0066909 A1 | 3/2008 | Hutchins et al. |
| 2008/0108524 A1 | 5/2008 | Willberg et al. |
| 2008/0115692 A1 | 5/2008 | Welton et al. |
| 2008/0230223 A1 | 9/2008 | McCrary et al. |
| 2008/0234129 A1 | 9/2008 | Asrar et al. |
| 2008/0261834 A1 | 10/2008 | Simon |
| 2009/0065253 A1 | 3/2009 | Suarez-Rivera et al. |
| 2009/0123699 A1 | 5/2009 | Maniar et al. |
| 2009/0145025 A1 | 6/2009 | Thrash |
| 2009/0176667 A1 | 7/2009 | Nguyen |
| 2009/0242833 A1 | 10/2009 | Chen et al. |
| 2009/0252789 A1 | 10/2009 | Trophardy |
| 2010/0071361 A1 | 3/2010 | Tandler et al. |
| 2010/0112200 A1 | 5/2010 | Barthel et al. |
| 2010/0189893 A1 | 7/2010 | Vitale et al. |
| 2010/0222242 A1 | 9/2010 | Huang et al. |
| 2010/0239642 A1 | 9/2010 | Campbell et al. |
| 2010/0248997 A1 | 9/2010 | Li et al. |
| 2010/0307749 A1 | 12/2010 | Nguyen et al. |
| 2010/0314114 A1 | 12/2010 | Moradi-Araghi et al. |
| 2011/0017677 A1 | 1/2011 | Evans |
| 2011/0079756 A1 | 4/2011 | Chun et al. |
| 2011/0098275 A1 | 4/2011 | Huang et al. |
| 2011/0118155 A1* | 5/2011 | Pisklak ............. C04B 20/1074 507/274 |
| 2011/0120719 A1 | 5/2011 | Soane et al. |
| 2011/0212834 A1 | 9/2011 | Andersch et al. |
| 2011/0245113 A1 | 10/2011 | Phatak |
| 2011/0245114 A1 | 10/2011 | Gupta et al. |
| 2011/0265376 A1 | 11/2011 | Thrash et al. |

(56) References Cited

U.S. PATENT DOCUMENTS

| | | |
|---|---|---|
| 2011/0289841 A1 | 12/2011 | Thrash |
| 2012/0037364 A1 | 2/2012 | Guan et al. |
| 2012/0080192 A1 | 4/2012 | Hendrickson et al. |
| 2012/0190593 A1 | 7/2012 | Soane et al. |
| 2012/0214714 A1 | 8/2012 | Whitwell et al. |
| 2012/0225800 A1 | 9/2012 | Hendrickson |
| 2012/0227967 A1 | 9/2012 | Shaikh et al. |
| 2012/0305254 A1 | 12/2012 | Chen et al. |
| 2013/0000900 A1 | 1/2013 | Kalgaonkar et al. |
| 2013/0005569 A1 | 1/2013 | Hendrickson et al. |
| 2013/0133251 A1 | 5/2013 | Thrash |
| 2013/0161003 A1 | 6/2013 | Makarychev-Mikhailov et al. |
| 2013/0233545 A1 | 9/2013 | Mahoney et al. |
| 2013/0274153 A1 | 10/2013 | Urbanek |
| 2014/0000891 A1 | 1/2014 | Mahoney et al. |
| 2014/0298722 A1 | 10/2014 | Thrash |
| 2015/0068747 A1 | 3/2015 | Hwang et al. |
| 2016/0251570 A1 | 9/2016 | Hook et al. |

FOREIGN PATENT DOCUMENTS

| | | |
|---|---|---|
| WO | 8501736 A1 | 4/1986 |
| WO | 1991013541 A1 | 9/1991 |
| WO | 2005071412 A2 | 8/2005 |
| WO | 2007086771 A1 | 8/2007 |
| WO | 2009018327 A2 | 2/2009 |
| WO | 2009078745 A1 | 6/2009 |
| WO | 2009102565 A1 | 8/2009 |
| WO | 2009123699 A2 | 9/2009 |

OTHER PUBLICATIONS

Drill & Fill Manufacturing. DF24—Drill & Fill Aerator Head Specifications. http://www.drillandfillmfg.com/drillfill.html. Accessed May 27, 2008.

Drill & Fill Manufacturing. D60—Drill Aerator Head Specifications. http://www.drillandfillmfg.com/drill.html. Accessed May 27, 2008.

Drill & Fill Manufacturing. Drill & Fill Aerification. http://www.drillandfillmfg.com/options.html. Accessed May 27, 2008.

Hogentogler & Co , Inc. Sieves: ASTM E-11 | AASHTO T-27. M-92. http://www.hogentogler.com/sieves/200mm_metric_sieves.htm. Accessed Dec. 11, 2007.

Graden USA. Inc. CSI Contour Sand Injection Specifications. http://www.gradenusa.com/_Sand_Injection.php. Accessed May 27, 2008.

Silica Fume Association. "What is Silica Fume?" http://www.silicafume.org/general-silicafume.html. Accessed May 27, 2008.

AZ Materials. Silica—Fumed Silica (Silicon Dioxide). http://www.azom.com/details.asp?ArticleiD=1386. Accessed May 27, 2008.

DryJect: Soil Amendments. http://www.dryject.com/dryject/profile.cfm. Accessed May 27, 2008.

DryJect: How it Works. http://www.dryject.com/dryject/howitworks/index.cfm. Accessed May 27, 2008.

Barascav D, Halliburton, retrieved Aug. 19, 2014 from http://www.halliburton.com/public/bar/contents/Data_Sheets/web/Product_Data_Sheets/A_through_C/BARASCAV_D.PDF, dated May 19, 2010.

Non-Final Office Action dated Dec. 21, 2015 in U.S. Appl. No. 14/293,555, 11 pages.

Non-Final Office Action dated Jan. 7, 2016 in U.S. Appl. No. 14/594,396, 10 pages.

Final Office Action dated Apr. 20, 2016 in U.S. Appl. No. 14/293,555, 8 pages.

Final Office Action dated Dec. 5, 2016 in U.S. Appl. No. 14/293,555, 8 pages.

Non-Final Office Action dated Dec. 21, 2016 in U.S. Appl. No. 14/594,396, 10 pages.

Non-Final Office Action dated Feb. 16, 2017 in U.S. Appl. No. 14/171,920, 11 pages.

Emulsions, Dewatered Emulsions, Dispersons Catalog, SNF FLOERGER, Oct. 2014, Andrezieux, France, 36 pages.

Non-Final Office Action dated Nov. 3, 2016 in U.S. Appl. No. 15/011,111, 11 pages.

Bava, L. et al., "Controlling the Processing Behavior of Silica Agglomerates Using a Thermoresponsive Binder", 2005, 11 pages. Retrieved from: http://www.nt.ntnu.no./users/skoge/prost/proceedings/aiche-2005/non-topical/Non%20topical/papers/411d.pdf.

Pourjavadi, Ali et al., "Synthesis, characterization, and swelling behavior of alginate-g-poly(sodium acrylate)/kaolin superabsorbent hydrogel composites", Journal of Applied Polymer Science, Sep. 2007, 10 pages. Retrieved from: https://www.researchgate.net/publication/229732407.

Notice of Allowance dated Aug. 2, 2016 in U.S. Appl. No. 14/594,396, 7 pages.

Non-Final Office Action dated Aug. 8, 2016 in U.S. Appl. No. 14/293,555, 8 pages.

Non-Final Office Action dated Apr. 21, 2017 in U.S. Appl. No. 14/293,555, 11 pages.

Non-Final Office Action dated May 10, 2017 in U.S. Appl. No. 15/136,352, 11 pages.

Final Office Action dated Jun. 29, 2017 in U.S. Appl. No. 15/011,111, 8 pages.

Final Office Action dated Jul. 12, 2017 in U.S. Appl. No. 14/594,396, 12 pages.

Final Office Action dated Nov. 17, 2017 in U.S. Appl. No. 15/136,352, 17 pages.

Non-Final Office Action dated Dec. 12, 2017 in U.S. Appl. No. 14/594,396, 13 pages.

Non-Final Office Action dated Jan. 5, 2018 in U.S. Appl. No. 14/171,920, 9 pages.

Final Office Action dated Aug. 14, 2017 in U.S. Appl. No. 14/171,920, 12 pages.

Final Office Action dated Sep. 11, 2017 in U.S. Appl. No. 14/293,555, 11 pages.

Notice of Allowance dated Oct. 18, 2017 in U.S. Appl. No. 15/011,111, 9 pages.

\* cited by examiner

HYDRAULIC FRACTURE COMPOSITION AND METHOD

RELATED APPLICATIONS

This application is a continuation of U.S. patent application Ser. No. 14/171,920, filed Feb. 4, 2014, which is a continuation of U.S. patent application Ser. No. 13/418,227, filed Mar. 12, 2012, now U.S. Pat. No. 9,057,014 issued Jun. 16, 2015; which is a continuation-in-part of U.S. patent application Ser. No. 13/299,288, filed Nov. 17, 2011, now U.S. Pat. No. 8,661,729 issued Mar. 4, 2014; which is a continuation-in-part of U.S. patent application Ser. No. 12/789,177, filed May 27, 2010, now U.S. Pat. No. 8,341,881 issued Jan. 1, 2013; which is a continuation of U.S. patent application Ser. No. 12/324,608, filed on Nov. 26, 2008 now U.S. Pat. No. 7,726,070, issued Jun. 1, 2010; which claims the benefit of U.S. Provisional Patent Application Ser. No. 61/012,912, filed Dec. 11, 2007; all of which are hereby incorporated by reference in their entirety.

BACKGROUND

1. The Field of the Invention

This invention relates to oil field and oil well development, and, more particularly, to novel systems and methods for fracturing and propping fissures in oil-bearing formations to increase productivity.

2. The Background Art

Oil well development has over one hundred years of extensive engineering and chemical improvements. Various methods for stimulating production of well bores associated with an oil reservoir have been developed. For example, United States Patent Application Publication US 2009/0065253 A1 by Suarez-Rivera et al. and entitled "Method and System for Increasing Production of a Reservoir" is incorporated herein by reference in its entirety and provides a description of fracturing technology in order to increase permeability of reservoirs. Moreover, various techniques exist to further improve the fracture channels, such as by acid etching as described in U.S. Pat. No. 3,943,060, issued Mar. 9, 1976 to Martin et al., which is likewise incorporated herein by reference in its entirety.

In general, different types of processes require various treatments. In general, well production can be improved by fracturing formations. Fracturing is typically done by pumping a formation full of a fluid, containing a large fraction of water, and pressurizing that fluid in order to apply large surface forces to parts of the formation. These large surface forces cause stresses, and by virtue of the massive areas involved, can produce extremely high forces and stresses in the rock formations. Accordingly, the rock formations tend to shatter, increasing porosity an providing space for the production oil to pass through the formation toward the bore hole for extraction. However, as the foregoing references describe, the chemistry is not simple, the energy and time required for incorporation of various materials into mixtures is time, money, energy, and other resource intensive.

It would be an advance in the art if such properties as viscosity, absorption, mixing, propping, and so forth could be improved by an improved composition and method for introduction.

BRIEF SUMMARY OF THE INVENTION

In view of the foregoing, in accordance with the invention as embodied and broadly described herein, a method, apparatus, and composition are disclosed in certain embodiments in accordance with the present invention, as including a substrate that may be formed of sand, rock product, ceramic sand, gravel, or other hard and structurally strong materials, provided with a binder to temporarily or permanently secure a hydrating polymer in proximity to the substrated. When used herein any reference to sand or proppant refers to any or all of these used in accordance with the invention. In certain embodiments of a method in accordance with the invention, a composition as described may be mixed directly into drilling fluids, such as a fracturing fluid made up of water and other additives.

By virtue of the increased surface area and weight provided to the polymeric powders affixed to the substrate, the surface area, and consequently the frictional drag, is greatly increased, sweeping the material of the invention into a flow of fluid. This greatly decreases the time required to absorb polymers into the fluid.

In fact, rather than having to wait to have the polymers thoroughly mixed, or absorb a full capacity of water, and thereby flow properly with the drilling fluid or fracturing fluid, a composition in accordance with the invention will sweep along with the fluid immediately, with the weight of the substrate submerging the polymer. Meanwhile, the cross sectional area presented results in hydrodynamic drag sweeps the composition along with the flow.

Meanwhile, over time, the polymeric powder adhered to the substrate will absorb water, without the necessity for the time, energy, temperature, mixing, and so forth that might otherwise be required by surface mixing. Thus, the composition in accordance with the invention is immediately transportable and flows, relying on the drilling or fracturing fluid as its carrier.

Moreover, as the polymer tends to pick up more water, the density of the granule of substrate and polymer powder becomes closer to the density of water. Accordingly, the size increase and the density change tend to drive the particles of the composition even more homogeneously with the flowing fluid. Thus, the sand does not settle out in various eddies, obstructions, and other locations of low velocity. Rather, the sand continues to be carried with the fluid, providing a double benefit. That is, the sand weight and area helps to initially mix and drive the particles (granules) with the fluid. Thereafter, the hydration of the polymer tends to increase the surface area and reduce the density of the granule or particle, tending to make the particles flow even better and more homogeneously with the surrounding fluid.

Ultimately, as the particles (granules) of the composition flow into fracture locations, they provide very small proppants as the substrate, such as sand, becomes trapped and lodged at various choke points. Nevertheless, because of the small size, the sand or other substrate acting as a proppant, simply needs to provide an offset, keeping fractured surfaces from collapsing back against one another. By providing the small, strong points of separation, the substrate provides a well distributed proppant, carried to maximum extent that the fluids will travel, and deposited in various traps, choke points, and the like.

The net saving in time, money, energy for heating and pumping, and the like is significant. Meanwhile, various technologies for reducing friction in the flow of fluid pumped into bore holes and other formation spaces is described in several patents, including U.S. Pat. No. 3,868,328, issued Feb. 25, 1975 to Boothe et al. and directed to friction reducing compounds, as well as U.S. Pat. No. 3,768,565, issued Oct. 30, 1973 to Persinski et al. and directed to friction reducing, U.S. Patent Application Publication US 2001/0245114 A1 by Gupta et al. directed to well servicing fluid, and U.S. Patent Application Publication US 2008/0064614 A1 by Ahrenst et al. and directed to friction reduction fluids, all described various techniques, materials, methods, and apparatus for developing, implementing, and benefiting from various well fluids. All the foregoing patent application publications and patents are hereby incorporated by reference.

Similarly, the development of various chemicals has been ubiquitous in oil field development. For example, U.S. Pat. No. 3,442,803, issued May 6, 1969 to Hoover et al. is directed to thickened friction reducers, discusses various chemical compositions, and is also incorporated herein by reference in its entirety.

In one embodiment of an apparatus, composition and method in accordance with the invention, a method may be used for formation fracturing. The formation may be in rock and within or near an oil reservoir underground. One may select an oil field region having a formation to be fractured. Fracturing may be sought to increase production. By providing a bore into the formation and a pump, a carrier material, typically comprising a liquid, and sometimes other materials dissolved or carried therein may be pumped into the formation through the bore.

The carrier as a liquid, or slurry comprising a liquid, or otherwise containing a liquid may be driven by the pump to be pressurized into the formation. However, the carrier may be provided an additive formed as granules. Each granule may include a substrate, such as a grain of sand, ceramic sand, crushed rock, other rock products, or the like having bonded thereto many particles (e.g. powder) formed from a polymer.

The polymer may be selected to have various properties, including lubricity, water absorption, water solubility, or the like. This hydrophilic polymer may be bonded permanently, temporarily, or the like to secure to the substrate. Various binders may be used alone or in combination. These may range from a solvent (e.g., organic or water) simply softening the polymer itself to bond it, to glues, sugars, molasses, and various other saccharides, as well as other products, including starches, other polymers, and so forth.

Thus, with some bonds, the polymer powder may be less permanent or attached to have a bond that is less robust. Over time, the polymer powder so attached may wear off, pull away, or otherwise remove from the substrate into the carrier fluid, and may even act as a viscous agent, lubricant, or the like in the carrier.

The method may include introducing the additive directly into the carrier. The more dense substrate will immediately submerge the granules in the carrier at ambient conditions. Thus heating, extensive mixing, waiting, and the like may be dispensed with, as the granules typically will not float or resist mixing once initial surface tension is broken.

Pumping the carrier toward the formation is possible immediately. The carrier fluid carries the granules by the liquid dragging against the substrate (with the particles of polymer attached. The substrate's cross sectional area engages immediately the surrounding liquid, dragging it into the carrier to flow substantially immediately therewith.

Meanwhile, weighting, by the substrate of the polymer, permits the granules to flow into and with the carrier independently from absorption of any of the liquid into the polymer. Nevertheless, over time, absorbing by the polymer a portion of the liquid results in the polymer expanding and providing by the polymer, lubricity to the carrier with respect to the formation;

Creating fractures may be accomplished by pressurizing the carrier in the formation. This creates fissures or fractures. Thus, flowing of the carrier and particles throughout the fractures or fissures in the formation results in lodging, by the particles, within those fractures or fissures. Unable to re-align, adjacent surfaces of rock, now fracture cannot close back together due to propping open the fractures by the substrate granules lodging in the fractures.

The substrate is best if selected from an inorganic material, such as sand, ceramic sand, or other hard, strong, rock product. The polymer may be selected from natural or synthetically formulated polymers. For example polymers of at acrylic acid, acrylate, and various amides are available. Polyacrylamide has been demonstrated suitable for all properties discussed above.

In fracturing a rock formation, the method may include providing an additive comprising a substrate formed as granules, each having an exterior surface, particles formed of a hydrophilic material, the particles being comminuted to a size smaller than the size of the granules and having first and second sides comprising surfaces. The granules may each be coated with the particles, the particles being dry and bonded to the exterior surface by any suitable binder, including the polymer softened with a solvent. The particles are each secured by the first side to the granules, the second side extending radially outward therefrom.

Upon identifying a reservoir, typically far underground from thousands of feet to miles, perhaps, and extending in a formation of rock, one needs to provide a bore into the formation. Providing a carrier, comprising a liquid, and possibly other materials known in the art, is for the purpose of fracturing the formation. Introducing the additive directly into the liquid at ambient conditions is possible, because the substrate weighs the granules down, and there is no need for long mixing, heating or the like as in addition of polymers directly to the carrier.

Thus, pumping may continue or begin immediately to move the carrier and additive down the bore and toward the formation. This results in exposing the second sides of the polymer powder particles directly to the liquid during transit of the carrier and additive toward and into the formation. The polymer particles thus begin absorbing, a portion of the liquid, typically principally water. Swelling of the polymer increases the size, effective diameter, and cross-sectional area, thus increasing the fluid drag on the granules.

Fracturing, typically by hydraulic pressure in the carrier creates fissures in the formation by fracturing the rock pieces in bending, or by layer separation, with tensile stresses breaking the rock. The resulting fissures allow carrying, by the carrier, of the granules into the fissures. However, fissures vary in size and path, resulting in lodging of granules, within the fissures. The granules do not settle out from the carrier, and thus may travel far into the formation and every fissure. However, each time a grain or granule is lodged like a chock stone, it obstructs the ability of the adjacent rock surfaces to close back with one another.

Thus, rather than the proppant (substrate) settling out ineffectually, failing to prop open the fissures, the granules are swept forcefully with the flow of the carrier wherever the carrier can flow, until lodged. Meanwhile, the lubricity of the polymer aids the granules, and thus the substrate from being slowed, trapped, or settled out by the slow flowing boundary layer at the solid wall bounding the flow.

In summary, weighting, by the substrate, sinks the polymer into the carrier readily and independently from absorption of the liquid into the polymer. Mixing, dissolving, and so forth are unnecessary, as the substrate drags the polymer into the carrier, and the carrier drags the granule along with it in its flow path. Lubrication is provided by the polymer between the substrate of each granule and adjacent solid walls of the bore, passages previously existing in the formation, and the fissures formed by fracturing. Any separating, by some of the powdered polymer particles from the substrate, still reduces friction drag on passage of the carrier and particles within the formation.

A composition for fracturing and propping a formation of rock may include a fluid operating as a carrier to be pumped into a rock formation, a substrate comprising granules of an inorganic material, each granule having an outer surface and a size characterized by a maximum dimension thereacross, and all the granules together having an average maximum dimension corresponding thereto. A polymer comprising a hydrophilic material selected to absorb water in an amount greater than the weight thereof may be bound to the substrate. The polymer is comminuted to particles, each particle having a size characterized by a maximum dimension thereacross.

All the polymer particles may be characterized by an average maximum dimension, and an effective (e.g. hydraulic diameter). The average maximum dimension of the particles is best if smaller, preferably much smaller, than the average maximum dimension of the granules.

The particles of the polymer, bound to the substrate, will travel with it in the fluid. Particles of the polymer are thus further directly exposed to water in the fluid during travel with the fluid. The granules, flowing in the fluid, are carried by the hydrodynamic drag of the fluid against the cross-sectional area of the granules coated with the particles of the polymer. The polymer, selected to expand by absorbing water directly from the fluid, increases the area and drag, assisting distribution in the formation by the carrier fluid. The polymer meanwhile operates as a lubricant lubricating the motion of the substrate against the formation during flow of the granules against solid surfaces in the formation, bore, and fracture fissures.

The inorganic material, such as sand, ceramic sand, or the like is typically sized to lodge in fissures formed in the formation and has mechanical properties rendering it a proppant capable of holding open fissures formed in the formation.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
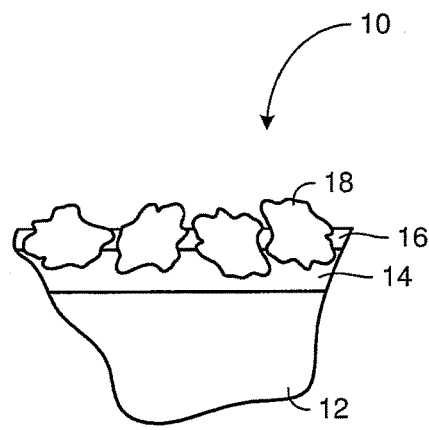
FIG. 1 is a schematic cross-sectional view of a material including a substrate provided with a binder securing a hydrating polymer thereto in accordance with the invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, a material 10 in accordance with the invention may include a substrate 12 formed of a suitable material for placement in the vicinity of a fracture region. For example, a substrate may be a particle of sand, ceramic sand, volcanic grit, or other hard material. In some embodiments, a substrate may be formed of organic or inorganic material. Nevertheless, it has been found effective to use sand as a substrate 12 inasmuch as it is submersible in water and will not float as many organic materials will when dry Likewise, the sand as substrate 12 is comminuted to such a small size that interstices between individual grains of the sand substrate 12 provide ample space and minimum distance for water to surround each of the substrate 12 particles.

In the illustrated embodiment, a binder 14 may be distributed as a comparatively thin layer on the surface of the substrate 12. Typical materials for binders may include both temporary and permanent binders 14. Permanent binders include many polymers, natural and synthetic. Temporary binders may be sugar-based or other water soluble materials. For example, corn syrup, molasses, and the like may form temporary binders. In the presence of water, such material may ultimately dissolve. Nevertheless, so long as the substrate 12 is not turned, mixed, or otherwise disturbed significantly, any other materials supported by the binder 14 would not be expected to dislocate.

Otherwise, certain naturally or synthetically occurring polymers may also be used as a binder 14. Lignicite may be used as a binder 14. Lignicite is a byproduct of wood, and provides material having good adhesive properties, and substantial permanence as a binder 14 on a substrate 12. Any suitable insoluble polymer may be used for more permanent binding.

Other polymers may be used to form a binder 14. For example, various materials used as glues, including mucilage, gelatin, other water soluble polymers including, for example, Elmer's™ glue, and the like may also operate as binders 14 to bind materials to a substrate 12.

In certain embodiments, the substrate 12 may be used in oil fields as a substrate 12 for polymer additives to fracture fluids. In other situations, the substrate 12 may be implemented as a proppant.

Pigment 16 may be implemented in any of several manners. For example, the substrate 12 may have pigment 16 applied prior to the application of the binder 14. In alternative embodiments, the pigment 16 may actually be included in the binder 14, which becomes a pigmented coating on the substrate 12. In yet other embodiments, the pigments 16 may be added to a hydration particle 18 either as a pigment 16 mixed therein, or as a pigment 16 applied as a coating thereto. Thus the location of the pigment 16 in the Figures is schematic and may take alternative location or application method.

Particles 18 of a hydrophilic polymer material may be bonded to the substrate 12 by the binder 14. Particles may be sized to substantially coat or periodically coat the substrate 12.

In certain embodiments, the hydrophilic material 18 may be a powdered polymeric material 18 such as polyacrylamide or any of the materials in the patent documents incorporated by reference. In other embodiments, the particles 18 may actually be organic material having capillary action to readily absorb and hold water. In one presently contemplated embodiment of an apparatus in accordance with the invention, the particles 18 may be powdered polymeric material in a dehydrated state, and having a capacity to absorb water, typically many times the weight (e.g., five to forty times) of a particular particle 18.

The substrate 12, in certain embodiments, may be some form of sand or granular material. The sand will typically be cleaned and washed to remove dust and organic material that may inhibit the binder 14 from being effective Likewise, the substrate 12 may be sized of any suitable size. For example, sand particles may range from much less than a millimeter in effective diameter or distance thereacross to approximately two millimeters across. Very coarse sands or ceramic sands may have even larger effective diameters. Hydraulic diameter is effective diameter (four times the area divided by the wetted perimeter). However, in one presently contemplated embodiment, washed and dried sand such as is used in construction, such as in concrete, has been found to be suitable. Fine sands such as masonry sands tend to be smaller, and also can function suitably in accordance with the invention.

Accordingly, the distance across each powder particle 18 may be selected to provide an effective coating of powdered particles 18 on the substrate 12. In one presently contemplated embodiment, the effective diameter of the particles 18 may be from about a 30 mesh size to about a 100 mesh size. For example, a sieve system for classifying particles has various mesh sizes. A size of about 30 mesh, able to pass through a 30 mesh sieve, (i.e., about 0.6 mm) has been found suitable Likewise, powdering the particles 18 to a size sufficiently small to pass through a 100 mesh (i.e., about 0.015 mm) sieve is also satisfactory. A mesh size of from about 50 mesh to about 75 mesh is an appropriate material to obtain excellent adhesion of particles 18 in the binder 14, with a suitable size of the particles 18 to absorb significant liquid at the surface of the substrate 12.

As a practical matter, about half the volume of a container containing a substrate 12 as particulate matter will be space, interstices between the granules of the substrate 12. One advantage of using materials such as sand as the substrate 12 is that a coating of the particles 18 may provide a substantial volume of water once the particles 18 are fully saturated. By contrast, where the size of the particles 18 is too many orders of magnitude smaller than the effective diameter or size of the substrate particles 12, less of the space between the substrate particles 12 is effectively used for storing water. Thus, sand as a substrate 12 coated by particles 18 of a hydrophilic material such as a polymer will provide substantial space between the substrate particles 12 to hold water-laden particles 18.

The diameter of the particles 18, or the effective diameter thereof, is typically within about an order of magnitude (e.g., 10.times.) smaller than the effective diameter of the particles of the substrate 12. This order of magnitude may be changed. For example, the order of magnitude difference less than about 1 order of magnitude (i.e., 10.times.) may still be effective. Similarly, an order of magnitude difference of 2 (i.e., 100.times.) may also function.

However, with particles 18 too much smaller than an order of magnitude smaller than the effective diameter of the substrate 12, the interstitial space may not be as effectively used Likewise, with an effective diameter of particles 18 near or larger than about 1 order of magnitude smaller than the size of the particles of the substrate 12, binding may be less effective and the particles 18 may interfere more with the substrate itself as well as the flow of water through the interstitial spaces needed in order to properly hydrate a material 10.

Figure 2:
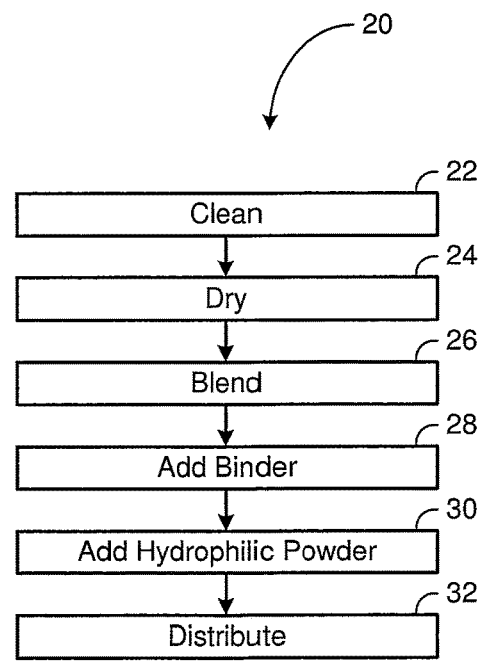
FIG. 2 is a schematic block diagram of one embodiment of a process for formulating and producing fluid additive particles in accordance with the invention.

Referring to FIG. 2, an embodiment of a process for formulating the material 10 may involve cleaning 22 the material of the substrate 12. Likewise, the material of the substrate 12 may be dried 24 to make it more effective in receiving a binder 14. The material of the substrate 12 may then be blended 26.

One embodiment, a ribbon blender provides an effective mechanism to perform continuous blending as the binder 14 is added 28. Other types of mixers, such as rotary mixers, and the like may be used. However, a ribbon blender provides a blending 26 that is effective to distribute binder 14 as it is added 28.

For example, if an individual particle of the substrate 12 receives too much binder 14, and thus begins to agglomerate with other particles of the substrate 12, a ribbon binder will tend to separate the particles as a natural consequences of its shearing and drawing action during blending 26.

As the binder 14 is added 28 to the mixture being blended 26, the individual particles of the substrate 12 will be substantially evenly coated. At this stage, the binder 14 may also be heated in order to reduce its viscosity and improve blending. Likewise, the material of the substrate 12 or the environment of the blending 26 may be heated in order to improve the evenness of the distribution of the binder 14 on the surfaces of the substrate 12 materials or particles 12.

Blending 26 of the binder 14 into the material of the substrate 12 is complete when coating is substantially even, and the texture of the material 10 has an ability to clump, yet is easily crumbled and broken into individual particles. At that point, addition 30 of the hydrophilic particles 18 may be accomplished.

For example, adding 30 the particles 18 as a powder into the blending 26 is a naturally stable process. Typically the particles 18 attach to the binder 14 of the substrate 12 particles, thus removing from activity that location. Accordingly, other particles 18 rather than agglomerating with their own type of material will continue to tumble in the blending 26 until exposed to a suitable location of binder 14 of the substrate 12. Thus, the adding 30 of the particles 18 or powder 18 of hydrophilic material will tend to be a naturally stable process providing a substantially even coating on all the particles of the substrate 12.

Just as marshmallows are dusted with corn starch, rendering them no longer tacky with respect to one another, the material 10 formulated by the process 20 are dusted with particles 18 and will pour freely. Accordingly, distribution 32 may be conducted in a variety of ways and may include one or several processes. For example, distribution may include marketing distribution from packaging after completion of blending 26, shipping to distributers and retailers, and purchase and application by users.

An important part of distribution 32 is the deployment of the material 10. In one embodiment of an apparatus and method in accordance with the invention, the material 10 may be poured, as if it were simply sand 12 or other substrate 12 alone. Since the powder 18 or particles 18 have substantially occupied the binder 14, the material 10 will not bind to itself, but will readily pour as the initial substrate material 12 will.

The material 10 may typically include from about 1 percent to about 20 percent of a hydrophilic material 18 or particles 18. The particles 18 may be formed of a naturally occurring material, such as a cellulose, gelatin, organic material, or the like.

In one embodiment, a synthetic gel, such as polyacrylamide may be used for the particles 18, in a ratio of from about 1 to about 20 percent particles 18 compared to the weight of the substrate 12. In experiments, a range of from about 5 to about 10 percent has been found to be the most effective for the amount particles 18.

Sizes of particles 18 may range from about 20 mesh to smaller than 100 mesh. Particles 18 of from about 50 to about 75 mesh have been found most effective.

The binder 14 may typically be in the range of from about in ¼ percent to about 3 percent of the weight of the substrate 12. A range of from about ¾ percent to about 1½ percent has been found to work best. That is, with a binder such as lignicite, ¼ of 1 percent has been found not to provide as reliable binding of particles 18 to the substrate 12. Meanwhile, a ratio of higher than about 3 percent by weight of binder 14 to the amount of a substrate 12, such as sand, when using lignicite as the binder 14, tends to provide too much agglomeration. The pouring ability of the material 10 is inhibited as well as the blending 26, due to agglomeration. Other binders also operate, including several smaller molecules that are water soluble. For example, glues, gelatins, sugars, molasses, and the like may be used as a binder 14. Insoluble binders are also useful and more permanent.

One substantial advantage for the material 10 in accordance with the present invention is that the material remains flowable as a sand-like material 10 into the fluids to be used in oil field fracturing. Thus, handling and application is simple, and the ability of granular material 10 to flow under and around small interstices of fractures provides for a very effective application.

Figure 3:
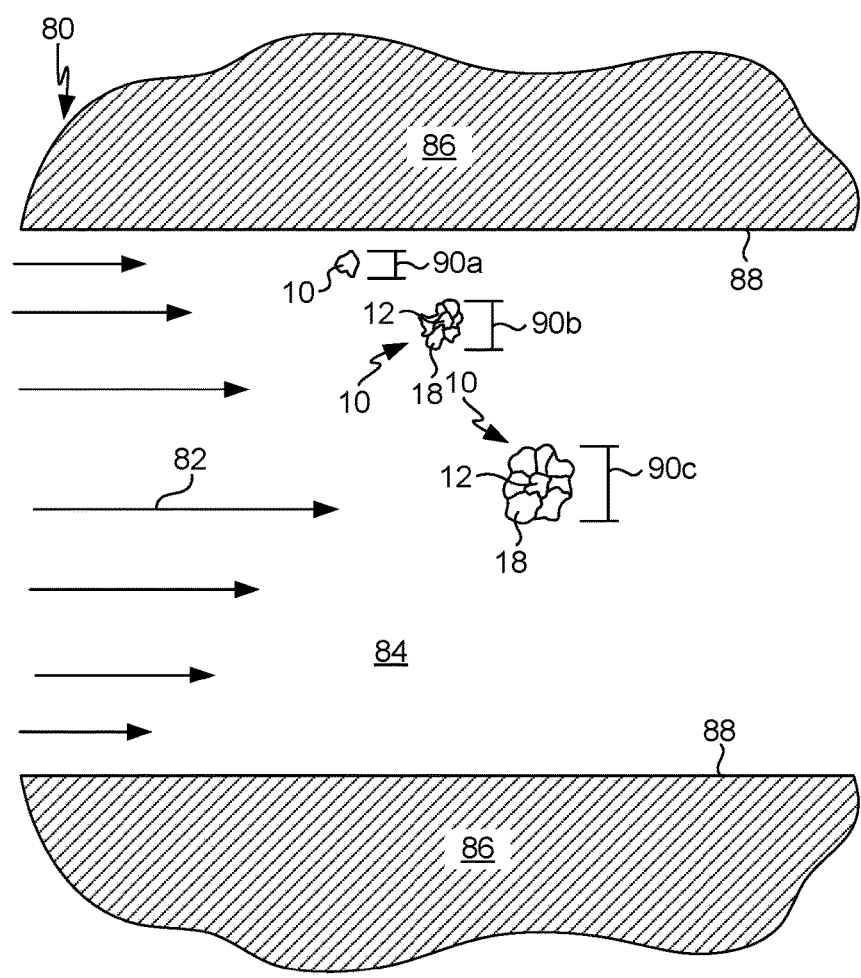
FIG. 3 is a schematic diagram of the fluid-particle interaction in an apparatus, composition, and method in accordance with the invention.

Referring to FIG. 3, a formation 80 such as a reservoir area of an oil may increase large and small flows 82 in passages 84 formed in the rock 86 of the formation 80. Typically, the flow 82 represented by arrows 82 indicating the development of flow at a faster speed in center of a passage 84, and the lower velocity near the wall 88 of the passage 84, illustrates the flow 82 of fluid in the passage 84.

In the illustrated embodiment, the granules 10 or large composite particles 10 or the materials 10 formed as a granulated material 10, having the substrate 12 in the center column with the polymer 18 adhered by a binder 12 on the outside thereof. This material 10 may be added to a flow 82 being pumped into a formation 80. Initially, a particle 10 will have an effective diameter 90a. In this condition, the particle 10 of material 10 is largely dependant on the density of the substrate 12, which constitutes the majority of its volume. Eventually, over time, with exposure to the liquid 82 or flow 82 and the water of that flow 82, the polymer 18 will absorb water, increasing in its effective diameter 90b. Ultimately, the polymer 18 or the polymer powder 18 will eventually become fully hydrated, increasing many times its size, and beginning to dominate the effective diameter 90c or hydraulic diameter 90c of the particle 10.

Initially, the diameter 90a reflects the comparatively smaller size and larger density of the particle 10 dominated by the weigh of the substrate 12, such as sand, ceramic sand, or some other hard and strong material. Ultimately, the diameter 90a or effective diameter 90a is sufficient to provide fluid drag according to fluid dynamic equations, drawing the particle 10 into the flow 82.

Meanwhile, the increase in diameter 90b and the ultimate effective diameter 90c result in reduction of the density of the particle 10 as the polymer 18 absorbs more water, bringing the net density of the particle 10 closer to the density of water. Accordingly, the particles 10 flow with the water exactly in sync, so to speak, rather than settling out as a bare substrate 12 would do.

For example, in areas where eddies in the flow occur, such as corners, crevices, walls, and the like, heavy materials having higher density, such as sand and the like, normally will tend to drift out of the flow, toward a wall 88, and ultimately will settle out. Instead, by virtue of the large "sail" presented by the larger diameter 90c of a fully hydrated polymer 18, each particle 10 stays with the flow 82 in passage 84, providing much more effective transport.

Figure 4:
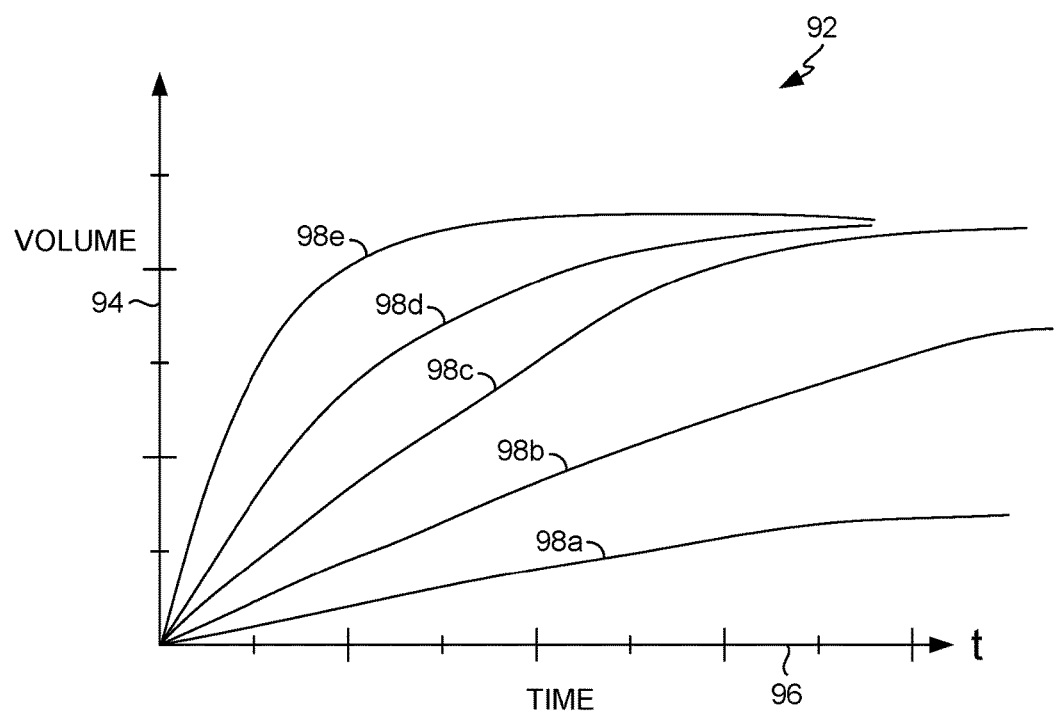
FIG. 4 is a chart illustrating qualitatively the relationship between volumetric increase over time at various temperatures, illustrating the improved activation with minimum mixing and temperature increase of particles in accordance with the invention.

Referring to FIG. 4, a chart 92 illustrates a volume axis 94 representing the volume of a particle 10 or material 10 in accordance with the invention. The volume axis 90 is displayed orthogonally with respect to a time axis 96, representing the passage of time of the particle 10 submerged in a carrier 82 or flow 82 of fluid 82. Typically, at different temperatures, illustrated by curves 98a-98e, with the temperature associated with curve 98a being the coldest and the temperature associated with the curve 98e being the hottest, one can visualize how heat added to a fluid flow 82 tends to increase the chemical activity and thus the rate of absorption of water into a polymer 18.

In an apparatus and method in accordance with the invention, the particles 10 may be added directly to a flow 82, without waiting for any significant time to absorb water into the polymer 18. Instead, the normal flow 82 will draw the particles 10 along in a passage 84 while exposing each individual particle 10 to surrounding fluid 82, thus promoting maximum rates of exposure and increased rates of absorption. Accordingly, the volume 94 increases, representing an increase in the absorption of water into the polymer 18.

In an apparatus and method in accordance with the invention, the curve 98a is suitable because the entire travel within the well bore, and within the formation 80 by the fluid 82 bearing the particles 10 is permissible and available as absorption time. By contrast, prior art systems rely on the increased temperature of curve 98e in order to provide the time, temperature, and mixing to work polymers into a flow 82 or liquid carrier 82.

Figure 5:
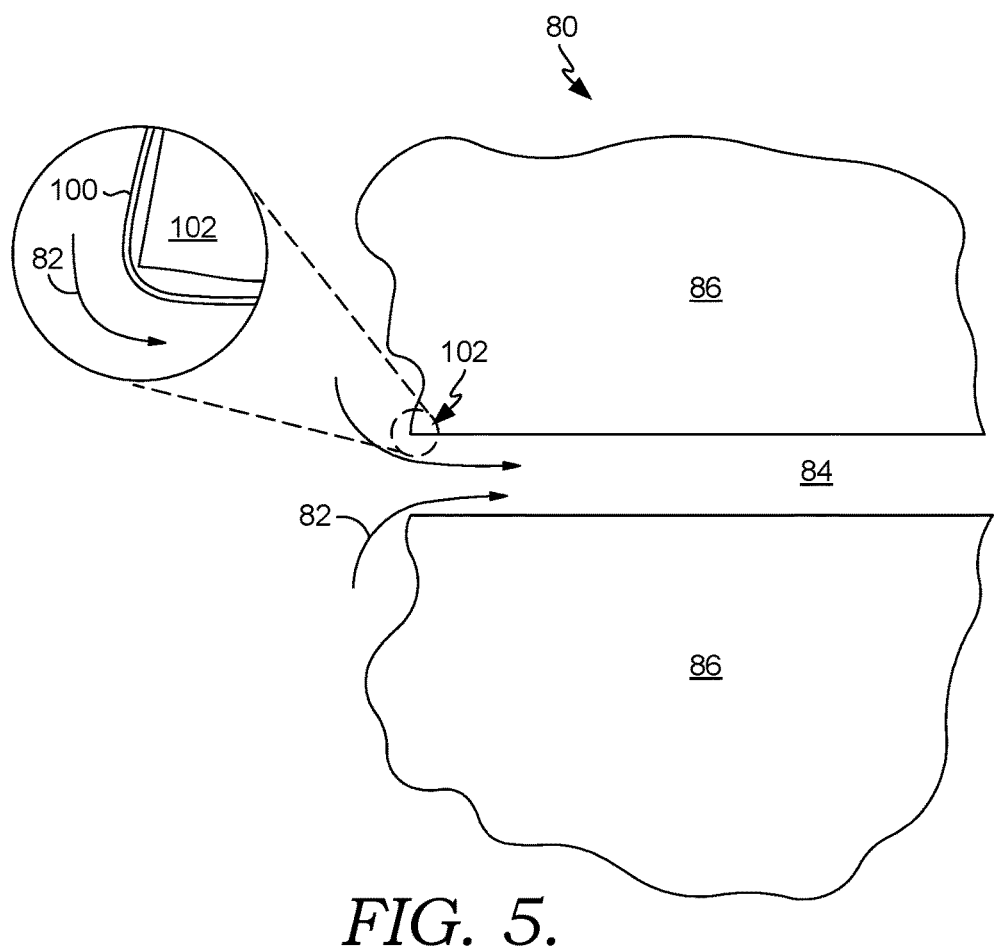
FIG. 5 is a schematic diagram illustrating one embodiment of friction reducing by polymers used in compositions in accordance with the invention.

Referring to FIG. 5, in one embodiment of an apparatus, composition, and method in accordance with the invention, some of the polymer 18 may eventually be scraped, sheared, or otherwise removed from the particles 10. If bonded only by itself with a water solvent, such a separation may be easier than if bonded by a more durable polymer. Such a release may even be engineered, timed, controlled by a solvent, or the like.

Thus, a certain amount of the polymer 18 may be released from the granule 10 into the carrier fluid 82 to flow with the fluid 82 and operate as a general friction reducer or provide its other inherent properties to the carrier fluid 82. By an engineered process of bonding and un-bonding, the polymer powder may be less permanent or attached to have a bond that is less robust. Over time, the polymer powder so attached may release, tear, wear off, pull away, or otherwise remove from the substrate into the carrier fluid to act as a viscosity agent, surfactant, lubricant, or the like in the carrier, according to its known properties available for modifying the carrier 82.

For example, a polymer 100 or polymer chain 100 may be captured on a corner 102 defining a passage 84 into which a flow 82 will proceed. Accordingly, the corner 102 renders less of an orifice on the passage 84 against entry of the flow 82 by virtue of the friction reduction of the polymer 100 in the fluid, deposited temporarily or permanently about a corner 102. Thus, other particles 10 passing the corner 100 may shear off a portion of the polymer 18 carried thereby or may rely on the presence of the polymer 18 as a direct friction reducing agent on the particle 10 (granule) itself, permitting the particles 10 to pass more easily with the flow 82 into the passage 84.

Figure 6:
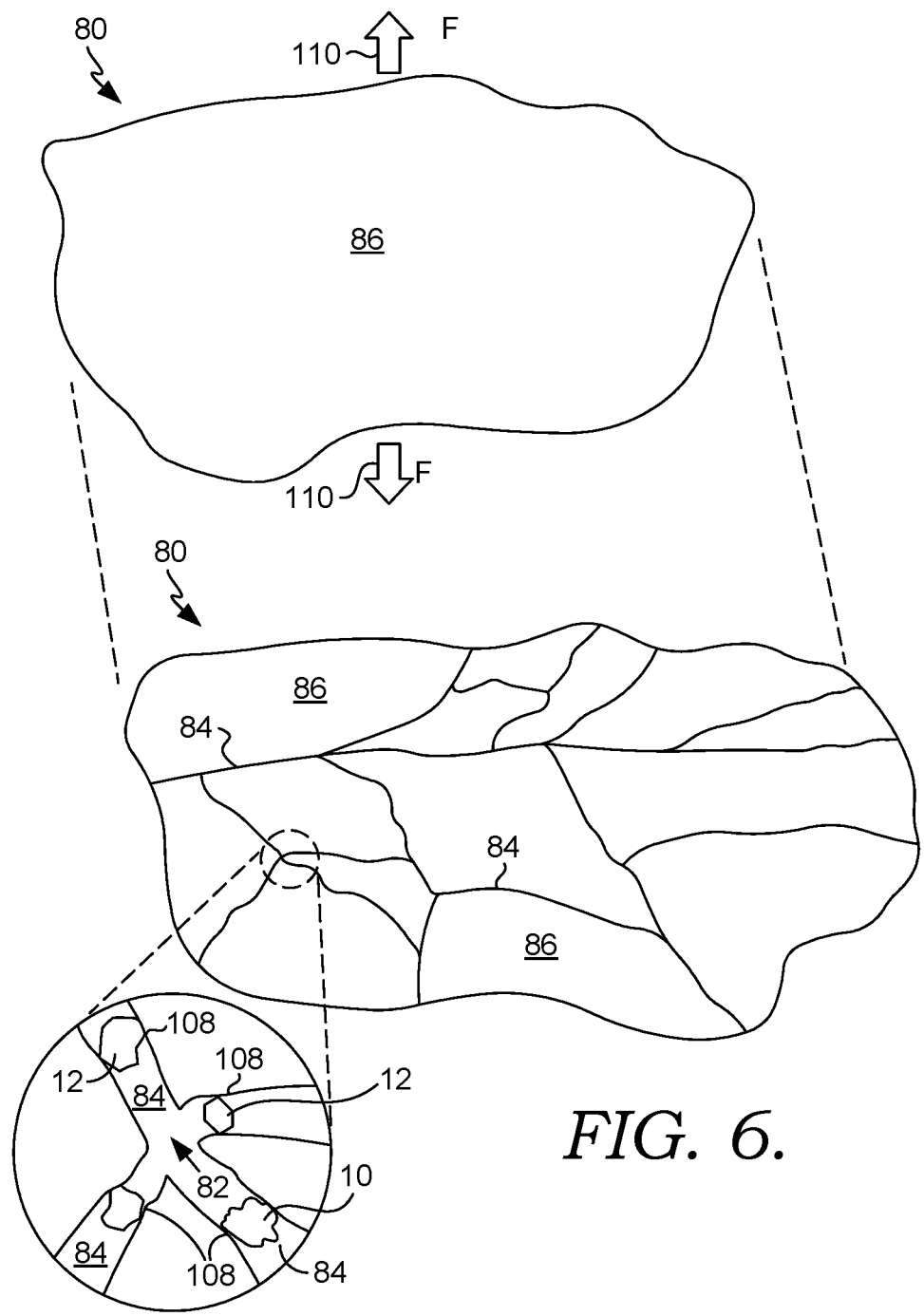
FIG. 6 is a schematic diagram of the fracturing and proppant action of particles in accordance with a method and composition according to the invention.

Referring to FIG. 6, the fracture process is described in various literature, including U.S. Patent Application publication US 2009/0065253 by Suarez-Rivera et al. incorporated herein by reference. In a fracturing process, the pressure applied to a formation 80 tends to force apart large expanses of rock. As a result of that expansion of passages 84 in a rock formation 80, the rock is stressed. Pressure pumped into the fluid 82 flowing in the passages 84 within the formation 80 results in bending stresses, tensile stresses, and so forth in the formation 80.

In FIG. 6, the forces 110 illustrated the effect of a large pressure applied over a large area. Since pressure multiplied by area equals force, applying an elevated hydraulic pressure to a large surface of a rock 86 or rock segment 86 within a formation 80 results in tensile forces. Compressive forces will not tend to break rock. However, a tensile force, which may be induced by bending, expansion, or the like, results in fracture of the rock. The fracture of the rock 86 thus results in condition shown in the lower view, in which the passages 84 are mere fissures within the rock 86.

The inset of FIG. 6 magnifies the fissures 84 or passages 84 formed in the rock 86 and immediately entered by the working fluid 82 being used for the fracture. Having the particles 10 formed around substrates 12, the fluid 82 extends into each of the fissures formed. Fissures 84 are simply passages 84. Some may be large, others small. Proppants 10 trapped in a small location may still maintain opened in another opening much larger elsewhere on the rock 86. They may also collect and fill larger spaces, eliminating the ability for rocks 86 to return to former positions.

After fracturing rock 86 to form all of the fissures 84, the fluid 82 will pass through the fissures, carrying particles 10, which eventually collect in cavities or reach choke points. In the absence of the particles 10, fissures 84 could close back up after the fracturing water leaves. However, by containing the particles 10, the individual substrates 12 are themselves rock in the form of sand, ceramic sand, or the like. Thus, a particle 10 need only obstruct the ability of the fissure 84 to close, and it may "prop" open the fissures 84 precluding the rock 86 or the pieces of rock 86 from settling back into alignment with one another.

Thus, the particles 10 both alone and in collected piles act as proppants left behind by the fluid flow 82, by virtue of the particles 10B captured. As a practical matter, it is only the substrate 12 that acts as a proppant. The polymer 18 may eventually be worn off but can easily be compressed, distorted, or cut. Regardless, as the fissures 84 open, they are back filled and close in at choke points and settling points collecting the substrate 12.

Figure 7:
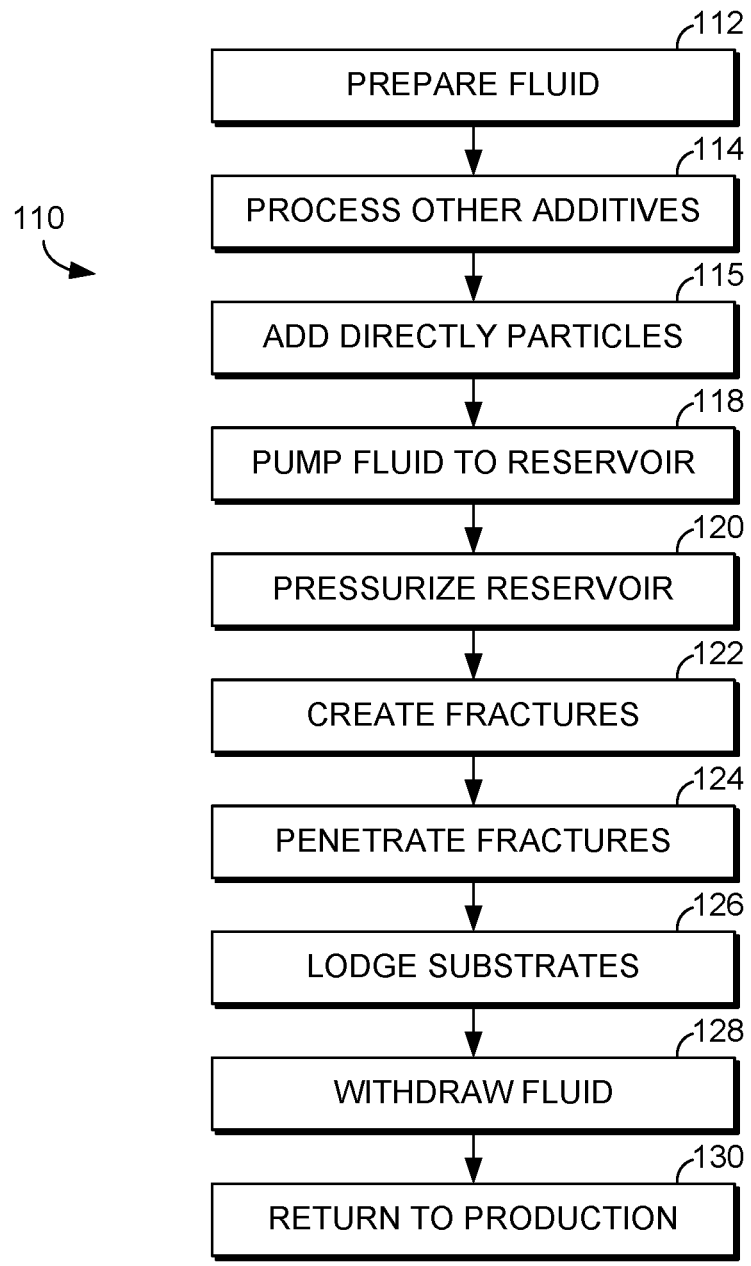
FIG. 7 is a schematic block diagram of a fracturing and propping process using compositions and methods in accordance with the invention.

Referring to FIG. 7, a process 10 may include preparing 112 a fluid 82. Processing 114 other additives other than the particles 10 may be done according to any suitable methods, including prior art processes. Adding 116 directly to the fluid 82, the particles 10 as described hereinabove, may be done in such a manner that the operators need not wait for absorption or any other processes to take place. Additional energy for elevating temperature is not required, neither mixing or the like, other than adding 116 directly particles 10 in to the flow 82. The flow 82 will immediately grab the particles 10 according the principles of fluid dynamics in which fluid drag is dependent upon a shape factor of the particle 10, the density of the fluid 82, the square of velocity of the fluid, and so forth, as defined in engineering fluid mechanics.

The fluid 82 now bearing the particles 10 would be immediately pumped 118 into the formation 80 that is the reservoir 80 of 8 and oil field. Eventually, pressurizing 120 the reservoir by pressurizing the fluid 82 results in creating 122 fractures 84 or fissures 84 within the formation 80 by breaking up the rock 86 of the formation 80. A fracture 84 with enough displacement may make a site for material 10 to stagnate and collect.

Creating 122 fracture lines throughout the formation 80 is followed by penetrating 124, by the particles 10 borne in the fluid 82 into the passages 84 or fissures 84 in the rock 86 of the formation 80. Whenever the flow 82 of fluid 82 carries a particle 10 to a choke point 108 in a passage 84, as illustrated in FIG. 6, a particle 10 will be lodged as illustrated in the inset of FIG. 6, a particle 10 with its polymer 18 still secured and intact may be lodged. Similarly, the substrate 12 may be lodged 126 and the polymer 18 may stripped therefrom by the consequent or subsequent flowing of material in the flow 82. Likewise, piles of stagnant particles 10 may backfill spaces, precluding rock 86 settling back in.

After the lodging 126 or propping 126 of the fissures 84 by the substrate 12, in the particles 10, the passages 84 will remain open. These fissures 84 may then be used tolater withdraw 128 the fluid 82 from the formation 80. Thereafter, returning 130 the formation 80 to production may occur in any manner suitable. For example, heat may be added to the formation, liquid may be run through the formation as a driver to push petroleum out, or the like.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A method for forming polymer-coated substrate particles, the method comprising:

mixing substrate particles with a synthetic binder so that at least a portion of the substrate particles are at least partly covered with the synthetic binder, the synthetic binder comprising a first volume of polyacrylamide wetted with a solvent, wherein a ratio of the synthetic binder to the substrate particles is from about 0.25 wt. % to about 3.0 wt. %;

coating the at least the portion of the substrate particles with a second volume of polyacrylamide in powdered form to form polymer-coated substrate particles; and drying at least a portion of the synthetic binder present on the polymer-coated substrate particles, wherein, when the polymer-coated substrate particles are submerged in water, at least a portion of the second volume of polyacrylamide is configured to swell, thereby increasing a fluid drag of the polymer-coated substrate particles compared to a fluid drag of the substrate particles so that the polymer-coated substrate particles are able to flow into a fissure by way of a carrier fluid and prop open the fissure so that the fissure remains open for extracting a fluid through the fissure.

2. The method according to claim 1, wherein the water-absorbing polymer comprises polyacrylate.

3. The method according to claim 1, wherein the substrate particles comprise sand.

4. The method according to claim 1, wherein the at least a portion of the second volume of polyacrylamide is configured to form a gel when exposed to water.

5. The method according to claim 1, wherein the outer polymeric coating comprises a co-polymer that includes an acrylamide, an acrylate, or a combination thereof.

6. The method according to claim 3, wherein the synthetic binder is configured to adhere the at least a portion of the second volume of polyacrylamide to at least a portion of the sand.

7. The method of claim 1, wherein a size of the substrate particles is at or between 30 to 100 mesh.

* * * * *

UNITED STATES PATENT AND TRADEMARK OFFICE
CERTIFICATE OF CORRECTION

PATENT NO.         : 10,040,990 B1
APPLICATION NO.    : 15/014623
DATED              : June 7, 2016
INVENTOR(S)        : Thrash et al.

It is certified that error appears in the above-identified patent and that said Letters Patent is hereby corrected as shown below:

On the Title Page

Item (72) Inventors, should read:
--Tommy K. Thrash, Lubbock, TX (US);
Calder Hendrickson, Lubbock, TX (US);
Todd Naff, Lubbock, TX (US)--.

Signed and Sealed this
Ninth Day of July, 2019

Andrei Iancu
*Director of the United States Patent and Trademark Office*